US00PP27018P3

(12) United States Plant Patent
Kievit

(10) Patent No.: US PP27,018 P3
(45) Date of Patent: Aug. 2, 2016

(54) ***SALVIA* PLANT NAMED 'BLUE MARVEL'**

(50) Latin Name: *Salvia nemorosa*
Varietal Denomination: Blue Marvel

(71) Applicant: Ball Horticultural Company, West Chicago, IL (US)

(72) Inventor: Christa Kievit, Hem (NL)

(73) Assignee: Ball Horticultural Company, West Chicago, IL (US)

( * ) Notice: Subject to any disclaimer, the term of this patent is extended or adjusted under 35 U.S.C. 154(b) by 185 days.

(21) Appl. No.: 14/121,358

(22) Filed: Aug. 25, 2014

(65) Prior Publication Data

US 2016/0057919 P1 Feb. 25, 2016

(51) Int. Cl.
*A01H 5/02* (2006.01)

(52) U.S. Cl.
USPC ..... Plt./475

(58) Field of Classification Search
USPC ..... Plt./475
See application file for complete search history.

*Primary Examiner* — Keith Robinson
(74) *Attorney, Agent, or Firm* — Audrey Charles

(57) ABSTRACT

A new and distinct cultivar of *Salvia* plant named 'Blue Marvel', characterized by its dark violet-colored flowers, medium green-colored foliage, and moderately vigorous, upright growth habit, is disclosed.

1 Drawing Sheet

Latin name of genus and species of plant claimed: *Salvia nemorosa.*

Variety denomination: 'Blue Marvel'.

BACKGROUND OF THE INVENTION

The present invention relates to a new and distinct cultivar of *Salvia* plant botanically known as *Salvia nemorosa* and hereinafter referred to by the cultivar name 'Blue Marvel'.

The new cultivar originated in a controlled breeding program in Hem, The Netherlands during August 2010. The objective of the breeding program was the development of *Salvia* cultivars having large flowers and compact growth habits.

The new *Salvia* cultivar is the result of cross-pollination. The female (seed) parent of the new cultivar is the proprietary *Salvia nemorosa* breeding selection coded H57-8, not patented, characterized by its dark blue-colored flowers, medium green-colored foliage, and moderately vigorous, upright growth habit. The male (pollen) parent of the new cultivar is the proprietary *Salvia nemorosa* breeding selection coded C7713-1, not patented, characterized by its light blue-colored flowers, medium green-colored foliage, and moderately vigorous, upright growth habit. The new cultivar was discovered and selected as a single flowering plant within the progeny of the above stated cross-pollination during June 2011 in a controlled environment in Hem, The Netherlands.

Asexual reproduction of the new cultivar by terminal stem cuttings since June 2011 in Hem, The Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Blue Marvel' as a new and distinct cultivar of *Salvia* plant:

1. Dark violet-colored flowers;
2. Medium green-colored foliage; and
3. Moderately vigorous, upright growth habit.

Plants of the new cultivar differ from plants of the female parent primarily in having a large flower size and from plants of the male parent primarily in a darker flower color.

Of the many commercially available *Salvia* cultivars, the most similar in comparison to the new cultivar is 'Haeumanarc', U.S. Plant Pat. No. 13,322. However, in side by side comparisons, plants of the new cultivar differ from plants of 'Haeumanarc' in at least the following characteristics:

1. Plants of the new cultivar have larger flowers than plants of 'Haeumanarc'; and
2. Plants of the new cultivar have larger leaves than plants of 'Haeumanarc'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Blue Marvel'. The plants were approximately three-months old from rooted cutting stage. They were grown in one-gallon containers for approximately two months in a greenhouse and one month outdoors in Elburn, Ill. Plants were given one pinch prior to transplant and one pinch two weeks after transplant.

DETAILED BOTANICAL DESCRIPTION

Figure 1:
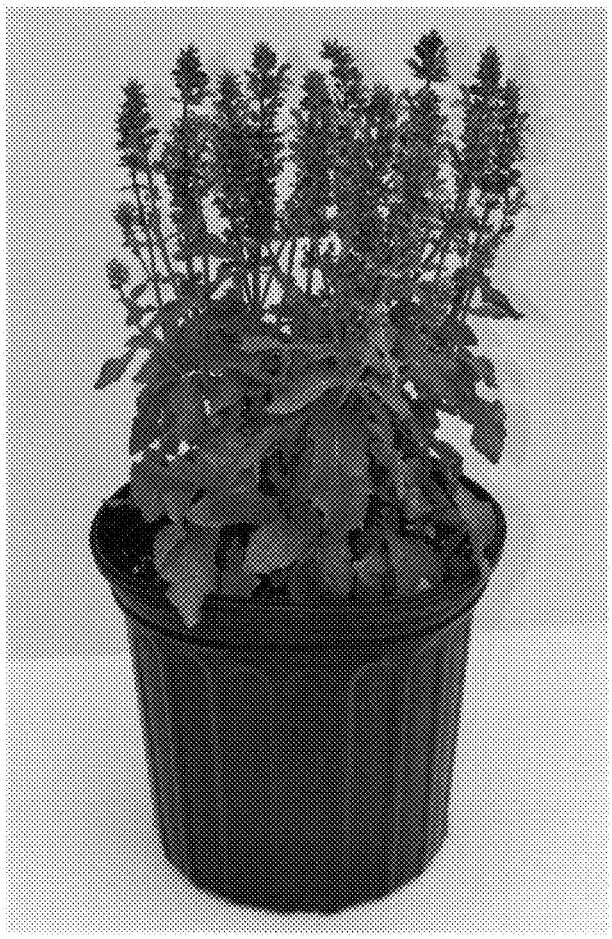
FIG. 1 illustrates a side view of the overall growth and flowering habit of 'Blue Marvel'.
Figure 2:
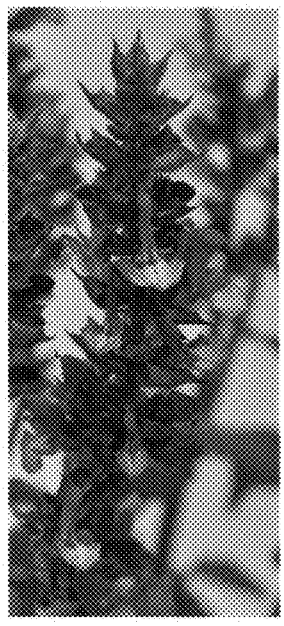
FIG. 2 illustrates a close-up view of an inflorescence of 'Blue Marvel'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in June 2014 under natural light conditions in West Chicago, Ill.

The following descriptions and measurements describe plants produced from cuttings from stock plants and grown under conditions comparable to those used in commercial practice. The plants were approximately three-months old from rooted cutting stage. They were grown utilizing a soilless growth medium in one-gallon containers for approximately two months in a greenhouse and one month outdoors in Elburn, Ill. Plants were given one pinch prior to transplant and one pinch two weeks after transplant. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Salvia nemorosa* cultivar Blue Marvel.

Parentage:

*Female parent.*—Proprietary *Salvia nemorosa* breeding selection coded H57-8, not patented.

*Male parent.*—Proprietary *Salvia nemorosa* breeding selection coded C7713-1, not patented.

Propagation:

*Type cutting.*—Terminal stem.

*Time to initiate roots.*—Approximately 12 to 15 days.

*Time to produce a rooted cutting.*—Approximately 35 to 42 days.

*Root description.*—Fine, fibrous, typically white to dark brown in color, actual color of the roots is dependent on substrate composition, water quality, fertilizer type and formulation, substrate temperature and physiological age of roots.

*Rooting habit.*—Freely branching.

Plant description:

*Commercial crop time.*—Approximately 12 to 14 weeks from a rooted cutting to finish in a 15 cm pot.

*Growth habit and general appearance.*—Moderately vigorous, upright growth habit.

*Plant type*.—Herbaceaous perennial.

*Hardiness*.—USDA zones 4a to 9b.

*Size.*—Height from soil level to top of plant plane: Approximately 32.0 cm. Width: Approximately 23.5 cm.

*Branching habit.*—Freely branching. Pinching enhances lateral branching. Quantity of branches per plant: Approximately 3 main basal branches and approximately 10 lateral branches.

*Branch.*—Shape: Square in cross section. Strength: Strong. Length to base of inflorescence: Approximately 11.5 cm. Diameter: Approximately 2.9 mm. Length of central internode: Approximately 4.5 cm. Texture: Densely pubescent. Color of young stems: 144B. Color of mature stems: 144B with occasional streaks of 187A, becoming woody 200C with age.

Foliage description:

*General description.*—Quantity of leaves per branch: Approximately 10. Fragrance: Strong, sage-like. Form: Simple. Arrangement: Opposite.

*Leaves.*—Aspect: Acute to perpendicular angle to stem. Shape: Ovate to elliptic. Margin: Crenate. Apex: Acute. Base: Cordate. Venation pattern: Pinnate. Length of mature leaf: Approximately 8.5 cm. Width of mature leaf: Approximately 3.8 cm. Texture of upper surface: Rugous, densely pubescent on venation. Texture of lower surface: Rugous, densely pubescent. Color of upper surface of young foliage: 138A with venation of 145D. Color of lower surface of young foliage: Closest to 138B with venation of: 145C. Color of upper surface of mature foliage: Closest to 137A with venation of 145C. Color of lower surface of mature foliage: Closest to 147B with venation of 145C.

*Petiole.*—Length: Approximately 1.7 cm. Diameter: Approximately 2.0 mm. Texture: Densely pubescent. Color: 146C.

Flowering description:

*Flowering habit.*—'Blue Marvel' is freely flowering under outdoor growing conditions blooming from spring through autumn and with limited flowering under short winter days in a greenhouse environment.

*Lastingness of individual floret.*—Approximately 4 to 5 days.

Inflorescence description:

*General description.*—Type: Spikes in verticillaster arrangement, florets in clusters of two, not persistent. Quantity of inflorescences per plant: Approximately 28. Fragrance: Faint, sweet. Length or height of inflorescence: Approximately 11.0 cm. Width of inflorescence: Approximately 3.0 cm. Quantity of fully-open flowers per inflorescence: Approximately 10 with up to 50 at peak flowering.

*Peduncle.*—Shape: Square in cross section. Strength: Strong. Aspect: Erect. Length: Approximately 3.5 cm. Diameter: Approximately 2.0 to 3.0 mm. Texture: Densely pubescent. Color: 138A.

Flower description:

*Type.*—Single, zygomorphic.

*Bud.*—Rate of opening: Generally takes 2 to 3 days for bud to progress from first color to fully open flower.

*Bud just before opening.*—Shape: Obovoid. Length: Approximately 8.0 mm. Diameter: Approximately 3.0 mm. Texture: Densely pubescent. Color: Calyx of 144B with venation of 187A; petals of N89B.

*Corolla.*—Shape: Bilabiate, lower lip having three lobes, based fused. Width: Approximately 7.0 mm. Length: Approximately 1.3 cm. Depth: Approximately 1.6 cm.

*Upper lip.*—Shape: Hooded. Margin: Entire. Apex: Rounded. Length from throat: Approximately 1.0 cm. Width: Approximately 1.0 mm. Texture of inner surface: Glabrous. Texture of outer surface: Sparsely pubescent. Color of inner surface when first and fully open: Closest to 92A. Color of outer surface when first and fully open: N88A to N88B.

*Lower lip.*—Shape of central lobe: Orbicular, cupped. Shape of lateral lobes: Elliptic to oblong. Margin: Entire. Apex of central lobe: Emarginate. Apex of lateral lobes: Acute. Length from throat of central lobe: Approximately 6.0 mm. Width of central lobe:

Approximately 8.0 mm. Length from throat of lateral lobes: Approximately 5.0 mm. Width of lateral lobes: Approximately 2.0 mm. Texture of upper surface: Glabrous. Texture of lower surface: Sparsely pubescent. Color of upper surface when first and fully open: N88B with center of 91C. Color of lower surface when first and fully open: 93C with center of 91D.

*Calyx.*—Shape: Tubular. Length: Approximately 6.0 mm. Diameter: Approximately 4.0 mm.

*Sepals.*—Quantity per flower: 4, fused. Shape: Elliptic. Apex: Acuminate. Margin: Entire. Length: Approximately 6.0 mm. Width: Approximately 2.0 mm. Texture of inner surface: Glabrous. Texture of outer surface: Sparsely pubescent. Color of inner surface: 137C. Color of outer surface: 144B with venation and margins of 187A.

*Bracts.*—Quantity: One bract located at the base of floret cluster. Texture of upper and lower surfaces: Densely pubescent. Color of upper and lower surfaces: 137C with 79A at tip.

*Pedicel.*—Strength: Strong, flexible. Aspect: At an acute angle. Length: Approximately 2.0 mm. Diameter: Less than 1.0 mm. Texture: Densely pubescent. Color: 145B with a heavy overlay of 187A.

*Reproductive organs.*—Androecium: Stamen quantity: 2 per flower, dorsifixed, strongly curved. Stamen length: Approximately 1.0 cm. Filament length: Approximately 8.0 mm. Filament color: N155D with and overlay of N88A, opaque. Anther shape: Narrowly elliptic to oblong. Anther length: Approximately 2.0 mm. Anther color: 200A. Pollen amount: Abundant. Pollen color: 8A. Gynoecium: Pistil quantity: 1 per flower, strongly curved. Pistil length: Approximately 1.6 cm. Stigma shape: Cleft, two-parted. Stigma length: 2.0 mm. Stigma color: N88A. Style length: Approximately 1.3 cm. Style color: NN155D, opaque with an overlay of N88A that fades toward ovary. Ovary length: Approximately 1.0 mm. Ovary color: 144C with 23A.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Blue Marvel', substantially as herein shown and described.

* * * * *